(12) United States Patent
Pedrazzini (10) Patent No.: US 9,519,847 B2
(45) Date of Patent: Dec. 13, 2016

(54) TRACEABLE LABELING APPARATUS FOR CONTAINERS OF BIOLOGICAL PRODUCTS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days.

(21) Appl. No.: 14/372,931

(22) PCT Filed: Jan. 14, 2013

(86) PCT No.: PCT/IB2013/050338
§ 371 (c)(1),
(2) Date: Jul. 17, 2014

(87) PCT Pub. No.: WO2013/108169
PCT Pub. Date: Jul. 25, 2013

(65) Prior Publication Data
US 2015/0002867 A1    Jan. 1, 2015

(30) Foreign Application Priority Data
Jan. 17, 2012   (IT) .............................. MI2012A0044

(51) Int. Cl.
*G06K 15/02*       (2006.01)
*G01N 35/00*       (2006.01)
(Continued)

(52) U.S. Cl.
CPC ....... *G06K 15/024* (2013.01); *G01N 35/00732* (2013.01); *G06F 3/1222* (2013.01);
(Continued)

(58) Field of Classification Search
USPC ...................................... 358/1.6, 1.15; 705/3
See application file for complete search history.

(56) References Cited

U.S. PATENT DOCUMENTS

2005/0141018 A1*   6/2005   Oak et al. ................... 358/1.15
2009/0048870 A1    2/2009   Godshall et al.
(Continued)

FOREIGN PATENT DOCUMENTS

EP    0380061 A1    8/1990
EP    0712525 A1    5/1996
(Continued)

*Primary Examiner* — Tammy Paige Goddard
*Assistant Examiner* — Keara Harris
(74) *Attorney, Agent, or Firm* — Jacobson Holman, PLLC.

(57) ABSTRACT

An apparatus for identifying a patient and marking containers of biological products or test tubes (13) associated with said patient before collecting said biological products to be analyzed is described, comprising a high security portable hardware device (1) for processing and storing the patient's data capable of associating the patient's personal data and biometric data, a reading and patient biometric recognition device (2) of said portable hardware device, a personal computer (4) interacting with an operator and connected to a local communications network (50) for exchanging information with remote data storage means (3), one or more computerized labeling machines (5) of test tubes (13), each comprising a printer (11) of barcodes onto labels (10) adapted to receive printing commands after comparing expected and detected specimens (13) accommodated in a positioning and recognition device (12) supported by said labeling machine (5) and applying said labels (10) to said test tubes (13). Each of said labeling machines (5) comprises a processing and control board (6) provided with a univocal address within said local communications network (50), which can be recalled by said operator by typing into a browser of said personal computer (4), said processing and control board (6) being capable of exchanging information with said remote data storage means (3) and with said personal computer (4), and on the basis of said information,
(Continued)

as well as that received after said comparison operated by said positioning and recognition device (12), of sending said print commands to said printer (11) included in said labeling machine.

11 Claims, 10 Drawing Sheets

(51) Int. Cl.
*G06F 19/00* (2011.01)
*G06F 3/12* (2006.01)
*G06K 15/00* (2006.01)

(52) U.S. Cl.
CPC .......... *G06F 3/1236* (2013.01); *G06F 3/1286* (2013.01); *G06F 19/366* (2013.01); *G06K 15/4045* (2013.01); *G06K 15/4095* (2013.01)

(56) References Cited

U.S. PATENT DOCUMENTS

| | | | |
|---|---|---|---|
| 2010/0044429 A1 | 2/2010 | Orkin | |
| 2011/0114263 A1* | 5/2011 | Pedrazzini | .................... 156/378 |
| 2011/0145006 A1* | 6/2011 | Pedrazzini | ........................ 705/2 |
| 2011/0173927 A1* | 7/2011 | Yamada | ................. G01N 35/04 |
| | | | 53/236 |

FOREIGN PATENT DOCUMENTS

| | | |
|---|---|---|
| EP | 1292937 A1 | 3/2003 |
| EP | 2313333 A1 | 4/2011 |
| WO | 94/22580 A1 | 10/1994 |
| WO | 95/04343 A1 | 2/1995 |
| WO | 01/99088 A1 | 12/2001 |
| WO | 2010/003880 A1 | 1/2010 |

* cited by examiner

TRACEABLE LABELING APPARATUS FOR CONTAINERS OF BIOLOGICAL PRODUCTS

The present invention relates to a traceable labeling apparatus for containers of biological products.

The need to develop a higher degree of automation and computerization of the process in which a patient has biological material collected in a hospital ward or laboratory following a doctor's prescription in order to have the collected specimen tested to thus provide a response concerning the patient's health is currently more and more felt.

With this regard, apparatuses are already known (see Patent Application PCT/EP2008/055280 by the Applicant) which can be conveniently integrated within a network architecture communicating with the Laboratory Information System (LIS) to receive orders from the LIS itself, which collects the patient's personal data and the list of tests that the patient must undergo, and thus perform operations compliant with such orders.

In particular, reference is made to the labeling of biological product containers (e.g. test tubes) during a step preceding that of collection, the latter being carried out by specialized hospital or laboratory personnel.

The existing apparatuses for this purpose receive information on each patient from the LIS, i.e. the personal data of the person who appeared at the hospital or laboratory as the result of a given medical prescription in order to undergo certain test types.

The Laboratory Information System may receive the list of such tests from the doctor in real time or not, whether the doctor is connected via a computerized system to the Booking Center; this would allow even the patient to skip the admission queue when appearing at the hospital/laboratory for the tests but, if this is not possible (i.e. if such an interaction is not available and therefore the patient is forced to register on-entered in the LIS database, which from that time onwards will contain the patient's complete personal profile as well as a list of all the tests that must be performed.

The patient then proves his/her identity at the collection area by means of a smart card or bracelet, and later the operator in charge of collecting will recall the identification form containing the patient's profile and the set of tests to be performed on his/her Personal Computer (PC).

At this point, a given number of test tubes are inserted in an apparatus like that described in the aforesaid Patent Application (i.e. a labeling machine) in order to have a label containing a barcode identifying the patient and the specific test type to which the specimen of biological material contained in the test tube will be subjected applied thereon.

The operation is repeated for all the various test tubes into which the patient's biological material must be separated, according to the number of tests that the patient must undergo, indicated by the LIS in accordance with the aforesaid medical prescription.

In the embodiment described in the aforesaid Patent Application by the Applicant, the step of test tube labeling follows that of biological material collecting. In this case, the test tubes already filled with biological material are labeled.

Problems appear in an architecture of this type because the operation managing application (software) is inside the PC on which the healthcare operator responsible for collection works (the operator typically being a phlebotomist, in the case of blood collection) and is thus installed on the PC itself to then communicate by means of a driver and a connection, e.g. of the USB type, with the labeling machine. Thereby, the entire procedure is bound to the use of that dedicated application, i.e. the application (typically supplied by the manufacturer of the whole apparatus) must be installed on each of the PCs in use by each of the operators.

Furthermore, the labeling machine—being the end instrument of the entire process, and precisely because the managing application is inside the operator's PC and thus outside the labeling machine itself—is a simple executor of orders which are supplied by the PC, which in turn receives information on each patient from the LIS.

Moreover, the operation of applying the barcode label onto the test tube may be inaccurate because of an imperfect coordination between when the label is materially detached from the wound ribbon which initially accommodates it and when it is applied onto the test tube, with the result that the label may be applied incorrectly, typically twisted or with the formation of folds when the label adheres onto the test tube.

Moreover, the possibility of tracking the specific time at which the single operations described above are performed is not included in the known systems.

It is an object of the present invention to provide an apparatus which allows to integrate the apparatuses which form it in a different manner from the known systems, so as to overcome the above-described problems; firstly, an object is to release the hospital or laboratory system from the constraints of installing a specific application on each PC provided for each of the operators in charge of collection, further ensuring that the labeling machine does not have an only passive role, i.e. is not a mere executor of orders imparted by means of the PC graphic interface.

A further object is to improve the application of the label on the test tube, so that this operation is performed to ensure a more accurate adhesion without imprecision.

A not last object consists in ensuring the possibility, during a single cycle of labeling various test rubes, of applying labels to test tubes also of various sizes, in response of the possible need to split the biological of the later processing of each of such test tubes by various machineries, and thus to carry out different types of tests.

A yet further object of the invention is to accurately keep track of the time at which each single operation is performed within the system. This may serve, if needed, as historical archive for retrieving information on the operation of each apparatus in the system; furthermore, considering that the test tubes are sent to the appropriate test devices after collection and labeling, such a feature may be useful for the doctor who analyzes the results of some tests performed on the biological specimen at a later time, helping to understand how long elapsed between collection and testing, and thus to decide whether the test may be significant or not according to the elapsed time.

In accordance with the invention, such objects are achieved by means of an apparatus for identifying a patient and marking containers of biological products or test tubes associated with said patient before collecting said biological products to be analyzed, comprising a high security portable hardware device for processing and storing the patient's data capable of associating the patient's personal data and biometric data, a reading and patient biometric recognition device of said portable hardware device, a personal computer interacting with an operator and connected to a local communications network for exchanging information with remote data storage means, one or more computerized labeling machines of test tubes, each comprising a printer of barcodes onto labels adapted to receive printing commands after comparing expected and detected specimens accommodated in a positioning and recognition device supported by said labeling machine and applying said labels to said test tubes, characterized in that each of said labeling machines comprises a processing and control board provided with a univocal address within said local communications network, which can be recalled by said operator by typing into a browser of said personal computer, with said remote data storage means and with said personal computer, and on the basis of said information, as well as that received after said comparison operated by said positioning and recognition device, of sending said print commands to said printer included in said labeling machine.

In accordance with the invention, such objects are further achieved by means of a labeling machine suitable for marking containers of biological products or test tubes, comprising a barcode printer on labels adapted to receive printing commands after comparing expected and detected test tubes accommodated in a positioning and recognition device supported by said labeling machine and to apply said labels onto said test tubes, characterized in that it comprises synchronization means between the operation of printing said label and the operation of rotating said test tube for applying said label thereto.

These and other features of the present invention will be further apparent from the following detailed description of an embodiment thereof, shown by way of non-limitative example in the accompanying drawings, in which.

The traceable labeling apparatus according to the invention (FIG. 1) comprises a patient's personal smart card 1 having a microprocessor with calculation and storage functions and a biometric identification device 2 capable of reading the patient's biometric data and the information contained in the smart card 1.

Figure 1:
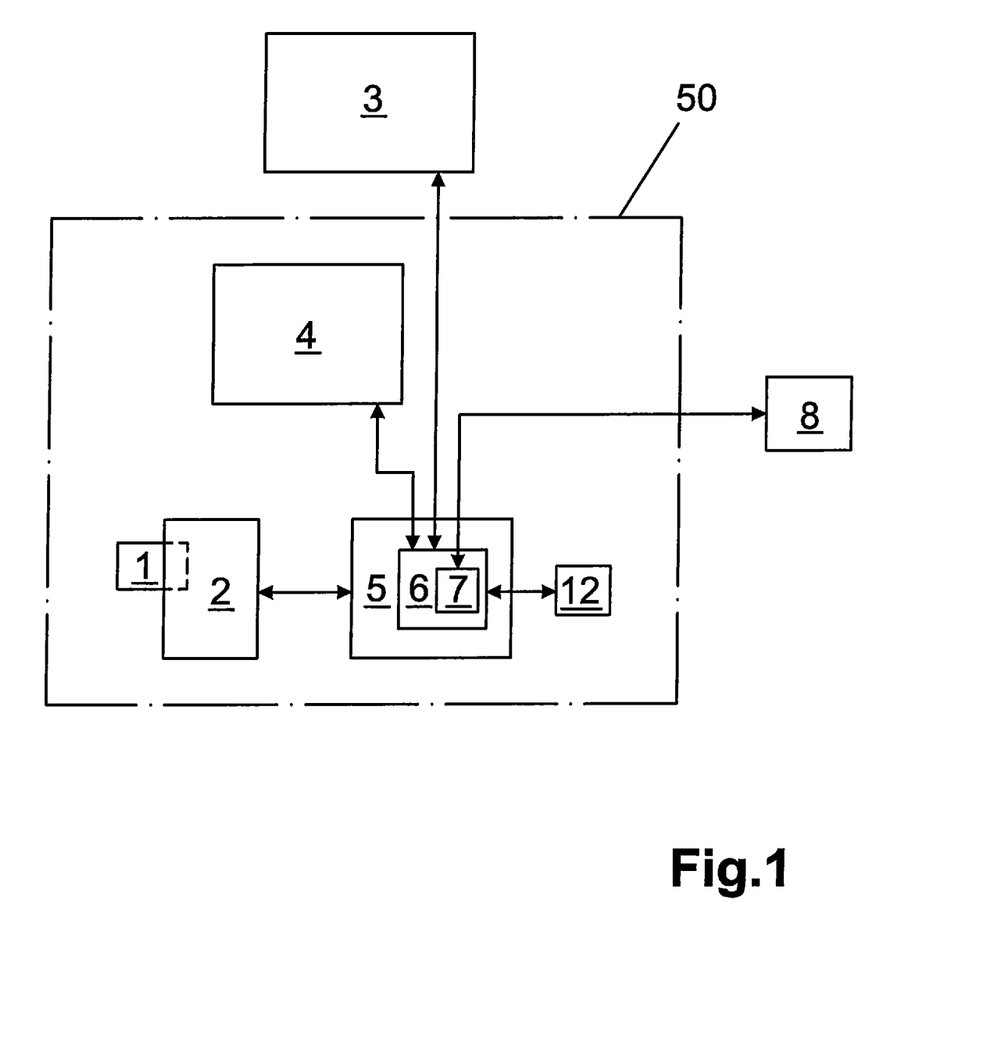
FIG. 1 is a block chart of the system architecture according to the invention.

Smart card 1 contains the patient's personal and biometric data. The personal data are also contained in a database 3 of a Laboratory Information System (LIS). The biometric data are instead stored only on smart card 1, and there is no trace of information in database 3. This ensures the patient's confidentiality.

A removable or non-removable bracelet as described in Patents EP0712525 and EP1292937 or any other portable hardware device having a microprocessor with calculation and storage functions may be used instead of smart card 1.

The biometric data may advantageously be one or more fingerprints, as well as the iris, facial or hand biometric data, or other patient's physical features.

The system in FIG. 1 further comprises a Personal Computer 4 provided with a navigation browser and an Internet connection to the database 3, and a labeling machine 5 connected to the biometric identification device 2.

Labeling machine 5 integrates a processing and control board 6 therein, provided with a univocal network address recallable by an Internet All the above-described system components are connected to a local computerized network 50 (Intranet), except for the database 3 of the LIS, which is external (remote).

A traceability engine 7 capable of communicating with an external server 8, according to the objectives which will be explained in greater detail below, is additionally present on the processing and control board 6.

Figure 3:
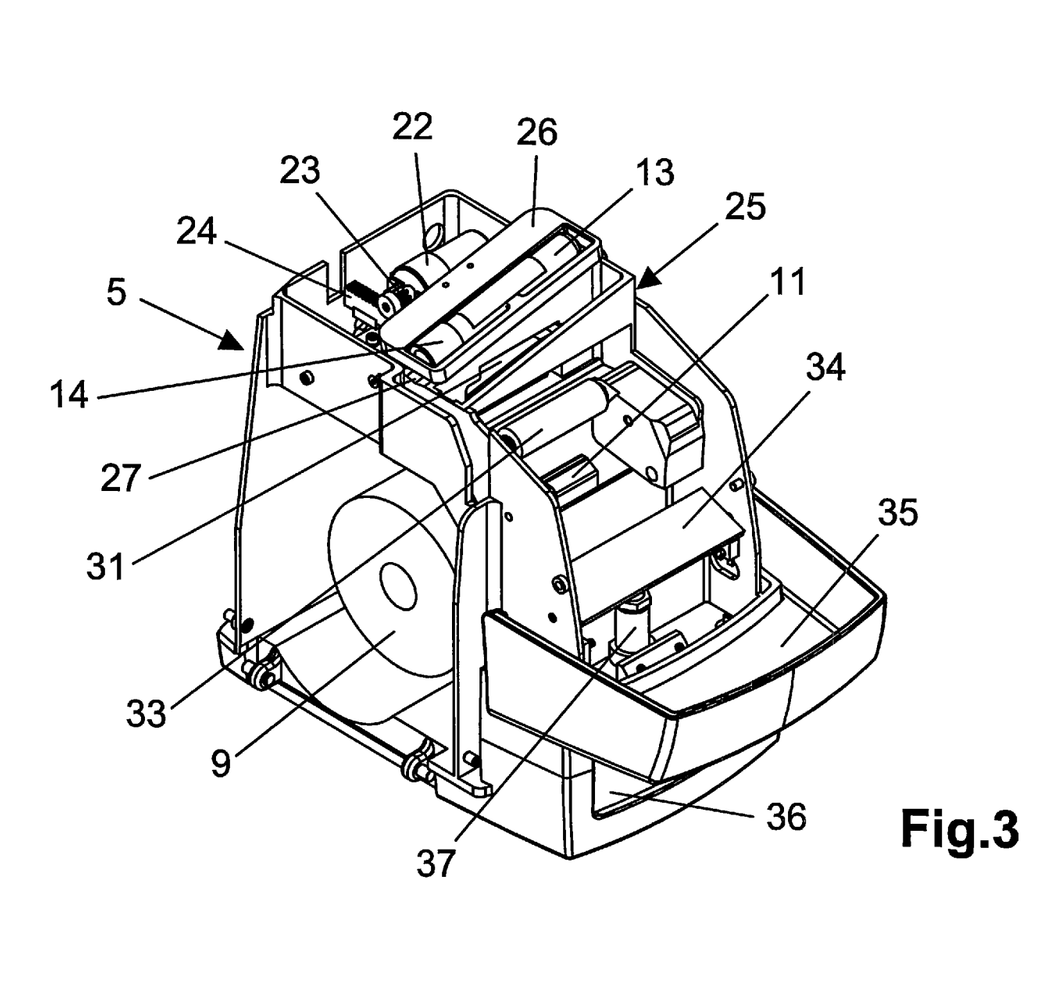
FIG. 3 shows again a perspective view the labeling machine, after having removed the outer casing.
Figure 8:
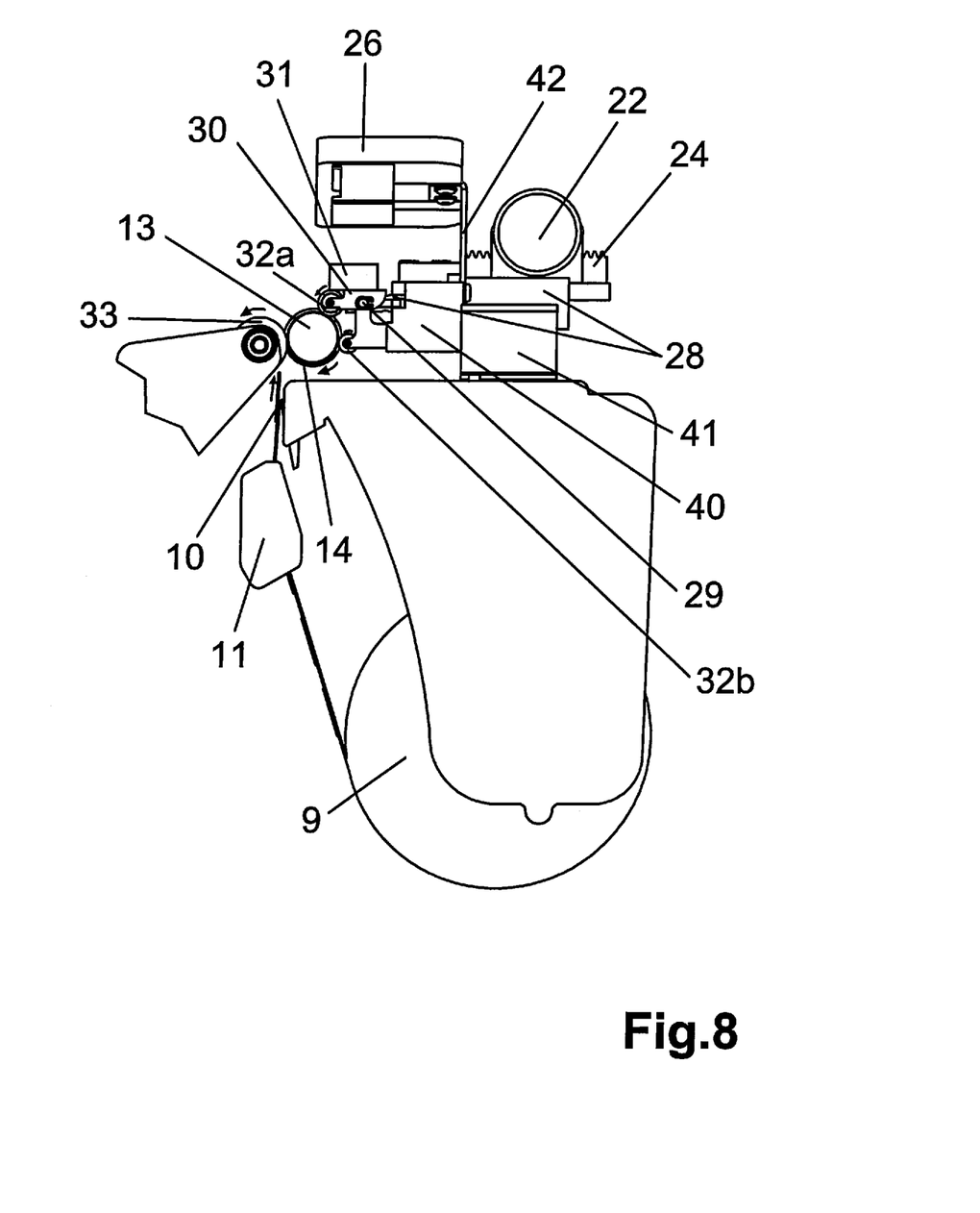
FIGS. 8 and 9 are side views again of two different steps of operation referred to the application of the label to the test tube.
Figure 9:
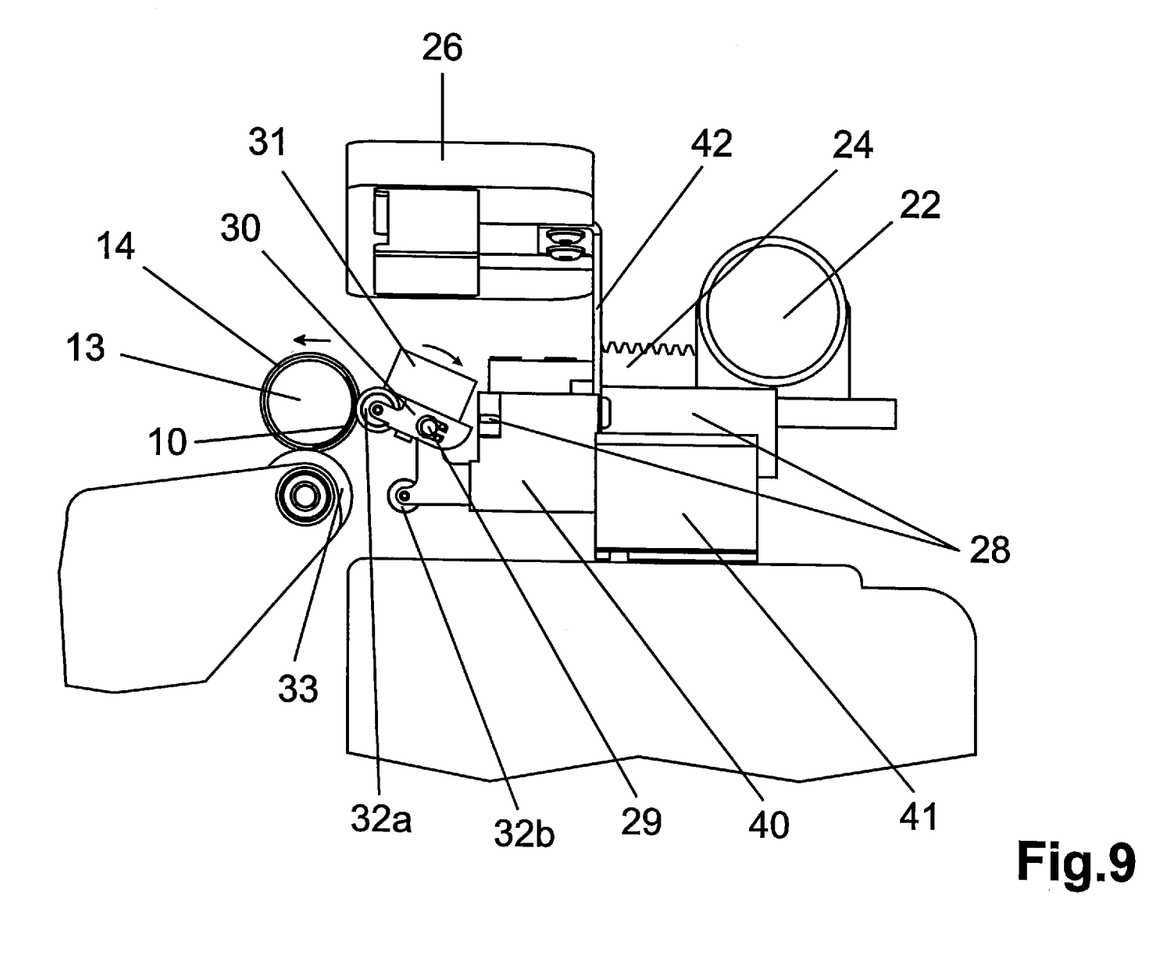

Furthermore, labeling machine 5 comprises a wound ribbon 9 of labels 10 (FIGS. 3 and 8), a barcode printer 11 and a positioning and recognition device 12 of a biological material container 13 (FIG. 4), preferably a test tube, closed by a colored cap 14 and suited to contain biological material (FIG. 3).

Device 12 (FIG. 4) comprises a first presence sensor 15 of test tube 13, positioned higher up, and a color sensor 16 of cap 14, a second presence sensor 17 (check sensor) of test tube 13, a presence sensor 18 of a pre-existing label and a length sensor 19 of test tube 13, all further down and integrated on a single board.

Figure 4:
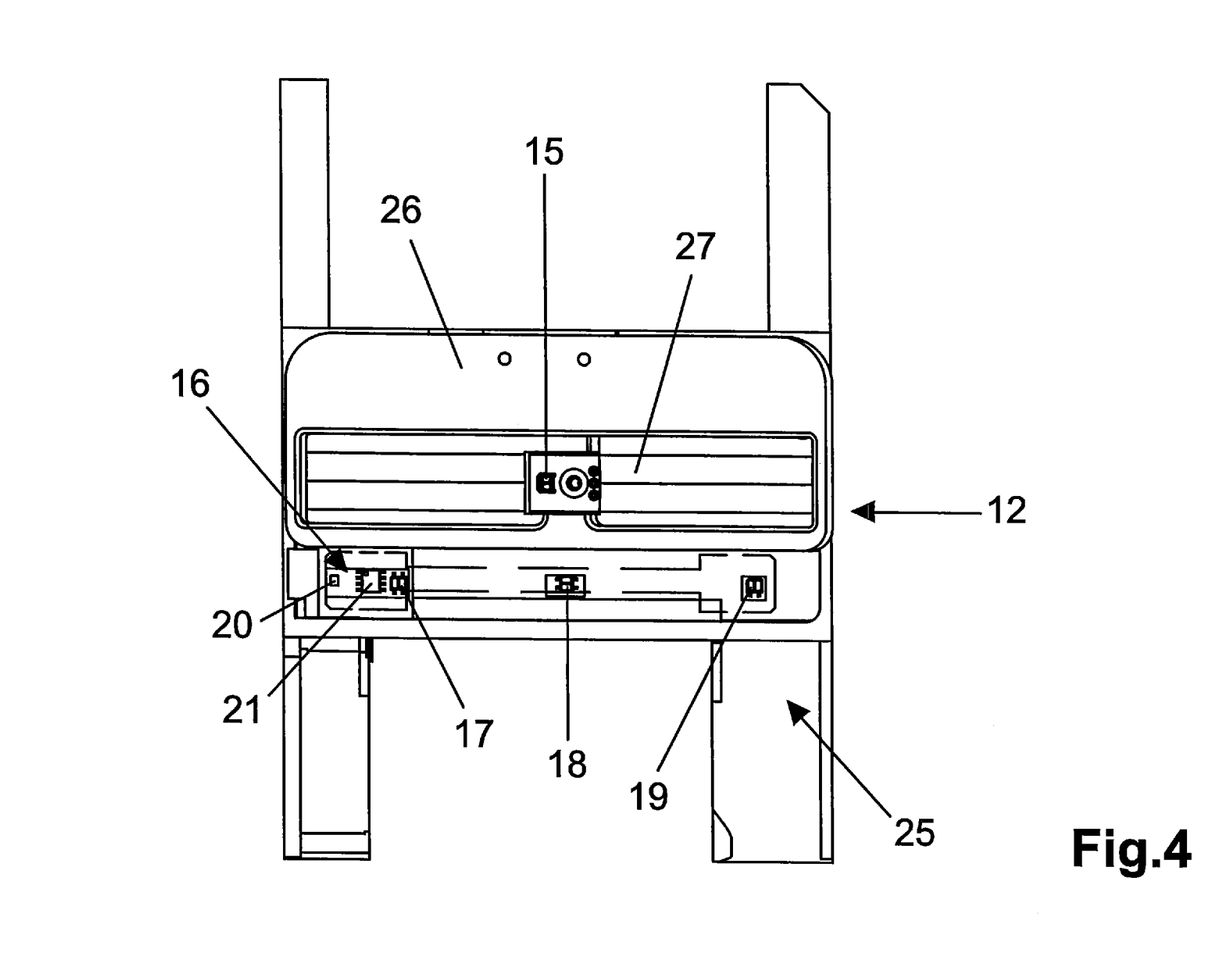
FIG. 4 is a top view of a detail of the positioning and recognition device after having removed the test tube.

Sensors 15, 17, 18 and 19 are of the reflective, infrared type, while sensor 16 comprises an emitter 20 and a receiver 21 and is based on a color converter consisting of four arrays of sixteen photodiodes, respectively equipped with a RGB (Red-Green-Blue) color filter.

An electric motor 22, which actuates a pinion 23 to engage a rack 24, fixed to a block 40, connected in turn both to an element 41 (provided with springs therein) and a vertical bracket 42 (FIG. 5), are further included within labeling machine 5 (FIG. 3).

A fixed structure body 25 is present (FIGS. 3, 5 and 6), with respect to which the aforesaid components, connected to one another, are integrally displaced.

An inclined compartment 26 (FIG. 5), which is shaped so as to accommodate the test tube 13 therein, is fixed to the vertical bracket 42. grooved housing 27 (FIGS. 3, 4 e 5) positioned under the opening of the inclined compartment 26. The "V" shape of such a housing 27 allows the test tube 13 to remain still while it rests thereon.

Figure 5:
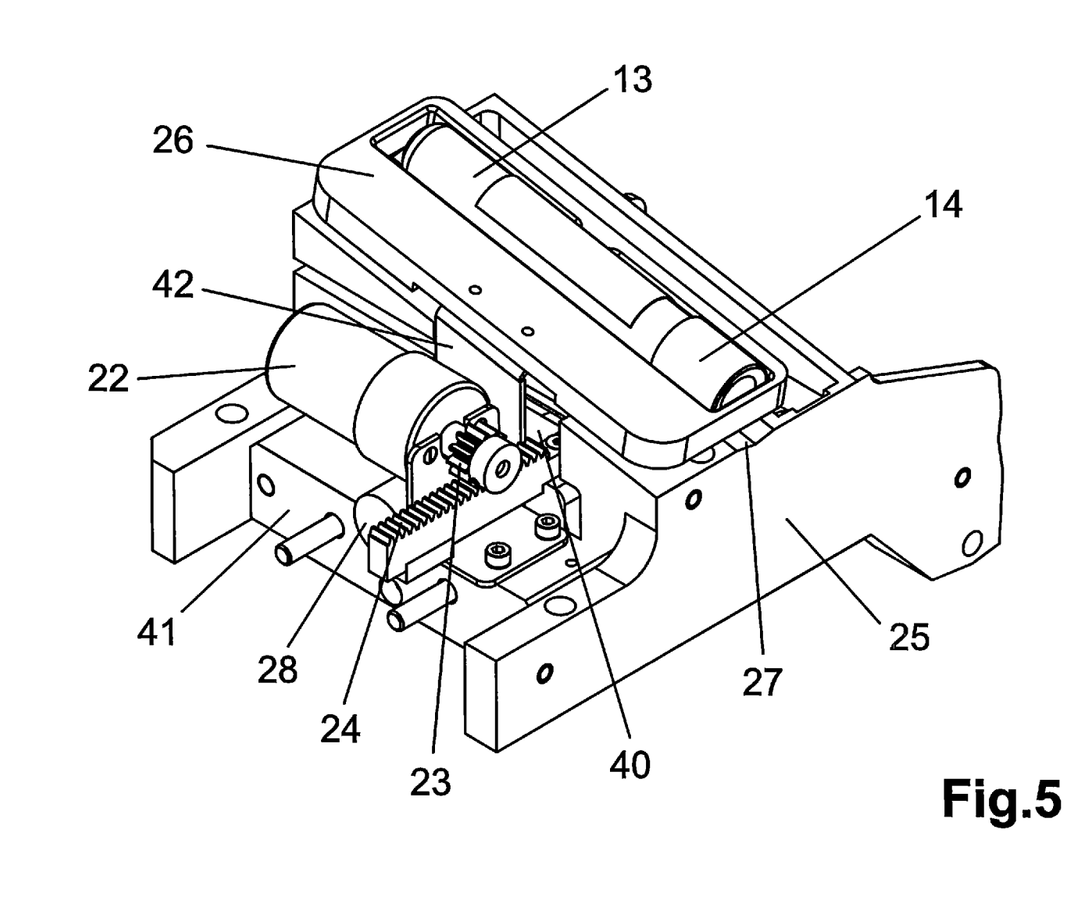
FIG. 5 shows a rear perspective view of a detail of some mechanical components, in particular those integral with the movement of the rack.

Furthermore, a first electromagnet 28, which passes through bracket 42 and block 40, is present close to rack 24 (FIG. 5). The electromagnet 28 can, according to the various steps of the operating cycle, either engage or not a pin 29 fixed at the ends of a shelf 30 on which an oblique chute 31 lays (FIGS. 6-9), which chute accommodates the test tube 13 once it falls, after the forward movement of the inclined compartment 26, through a hole obtained in the upper part of the structure body 25 (FIG. 3).

Furthermore, there are two passive secondary rollers 32a and 32b, and a motorized main roller 33, larger than the secondary rollers (FIGS. 6-9). The roller system is present to rotate the test tube 13 in order to apply the label 10, as will be explained in greater detail below.

Pin 29, shelf 30, oblique chute 31 and the two passive rollers 32a and 32b also move forwards and backwards integrally with block 40, and thus with rack 24, element 41, bracket 42 and inclined compartment 26.

Furthermore, the labeling machine 5 comprises a lever 34 (FIGS. 2 and 3), which—at the end of the processing of each single test tube 13—routes the test tube either towards a first collection tray 35 for correctly labeled test tubes or alternatively towards a second tray 36 for collecting the rejected test tubes. In the first case, the release of a second solenoid magnet 37 from a pin 38 (FIG. 10) is required.

Figure 2:
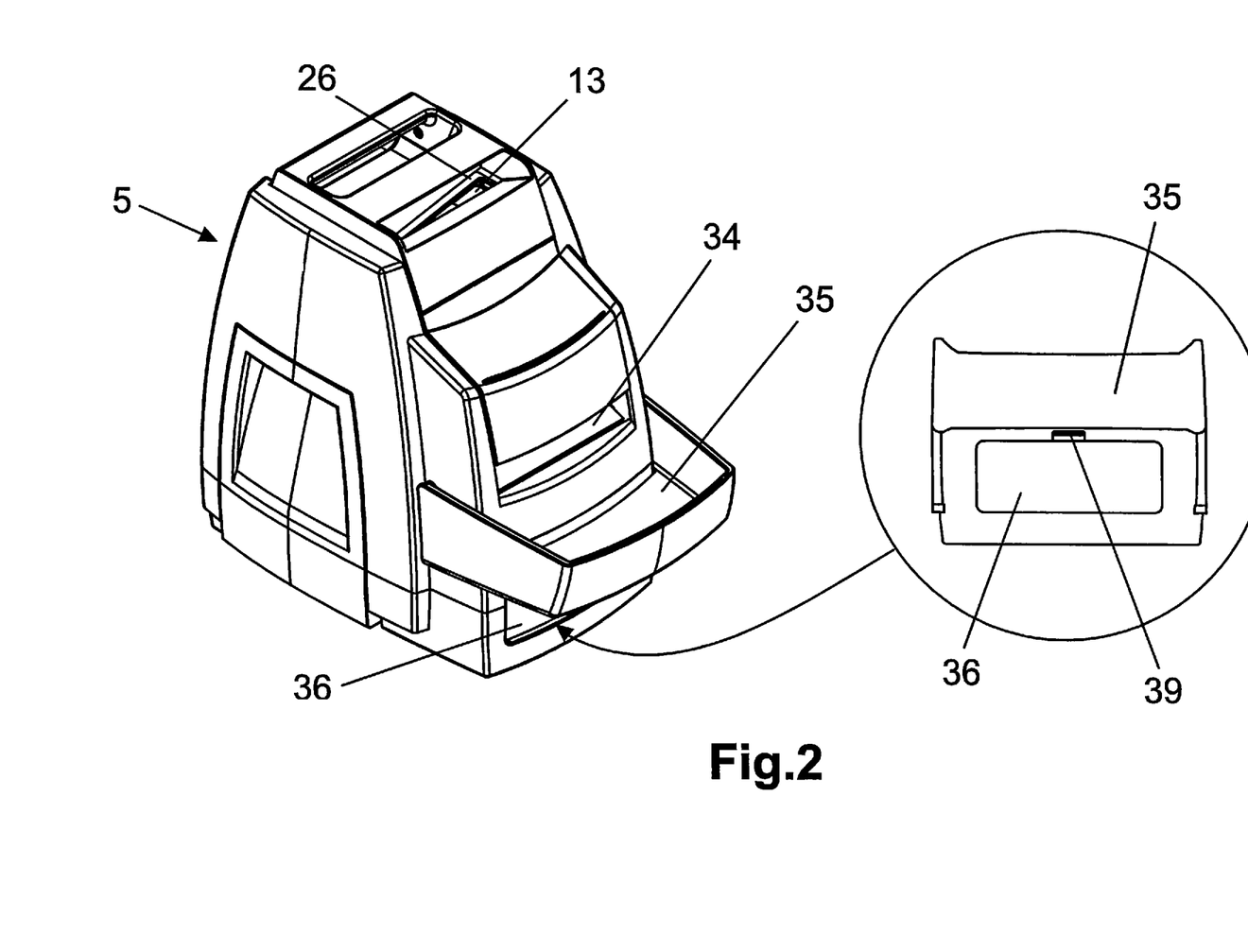
FIG. 2 shows a perspective view of the outer casing of the labeling machine.

Finally, a barcode reader 39 is present, under which each single test tube 13 passes after the collection, to confirm end of operation on the test tube 13 itself (FIG. 2).

The procedure steps referred to identifying the patient at the laboratory or hospital where the patient appeared to have biological material collected follow those disclosed in the above-mentioned patent application by the Upstream of this procedure, the smart card 1 with the patient's personal and biometric data is created and assigned to the patient, and later the patient, as prescribed by the doctor, appears at the laboratory admission to enter the prescription data; the data may have been previously received via computerized system if, as mentioned, the doctor's office is connected to the Booking Center: this would allow the patient to skip the admission queue of the laboratory/hospital and go directly to the collection point.

When it is his/her turn, the patient will provide positive identification by inserting smart card 1 in the biometric identification device 2 and so authenticating his/her personal and clinical data with his/her biometric data.

If the biometric data detected in real time on the patient by device 2 coincides with those on the smart card 1 (positive authentication of the patient), the application, i.e. the processing and control board 6 integrated in the labeling machine 5 present in the collection point (which is advantageously connected via USB to device 2), queries the database 3 of the LIS twice, firstly to also recall the patient's personal data from the database 3, and then to extract the list of tests to be performed (entered into database 3 during the step of admission) associated with the patient. This step thus highlights the active role of the labeling machine 5, performed in particular by the application residing on the processing and control board 6, which actively queries the database 3 of the LIS and does not only execute orders.

Once this step has been completed, the processing and control board 6 makes a message appear on the video of the monitor of PC 4 provided for the operator, indicating the patient's positive identification as well as the following information:

list of tests to be performed,
number and type of tests tubes 13 (differentiated by size and color of the cap) to be filled with biological material according to the
a target cap color of the test tube and the test tube size (long or short) is associated with each test in the list,
some of the patient's personal data.

After having obtained this information, the operator positions one or more empty test tubes 13 to be labeled in the inclined compartment 26 positioned in the upper part of the labeling machine 5 (FIGS. 2 and 3). The test tube 13 may be any one of those listed, i.e. there is no predetermined entry order of test tubes according to the list; in brief, it will suffice for the test tube to belong to the aforesaid list for it to be identified (and subsequently correctly labeled) later on by the sensors. The test tube 13 must be inserted with the cap 14 facing downwards, as shown in the FIG. 3. It is worth noting that several test tubes 13 can be positioned in the inclined compartment 26, but the labeling includes processing of one test tube 13 at a time, as will be explained in greater detail below.

The test tube rests in the grooved housing 27 which is located under the opening of the compartment 26 during this step. The test tube remains still in the housing 27 by virtue of the latter's "V" shape.

Figure 6:
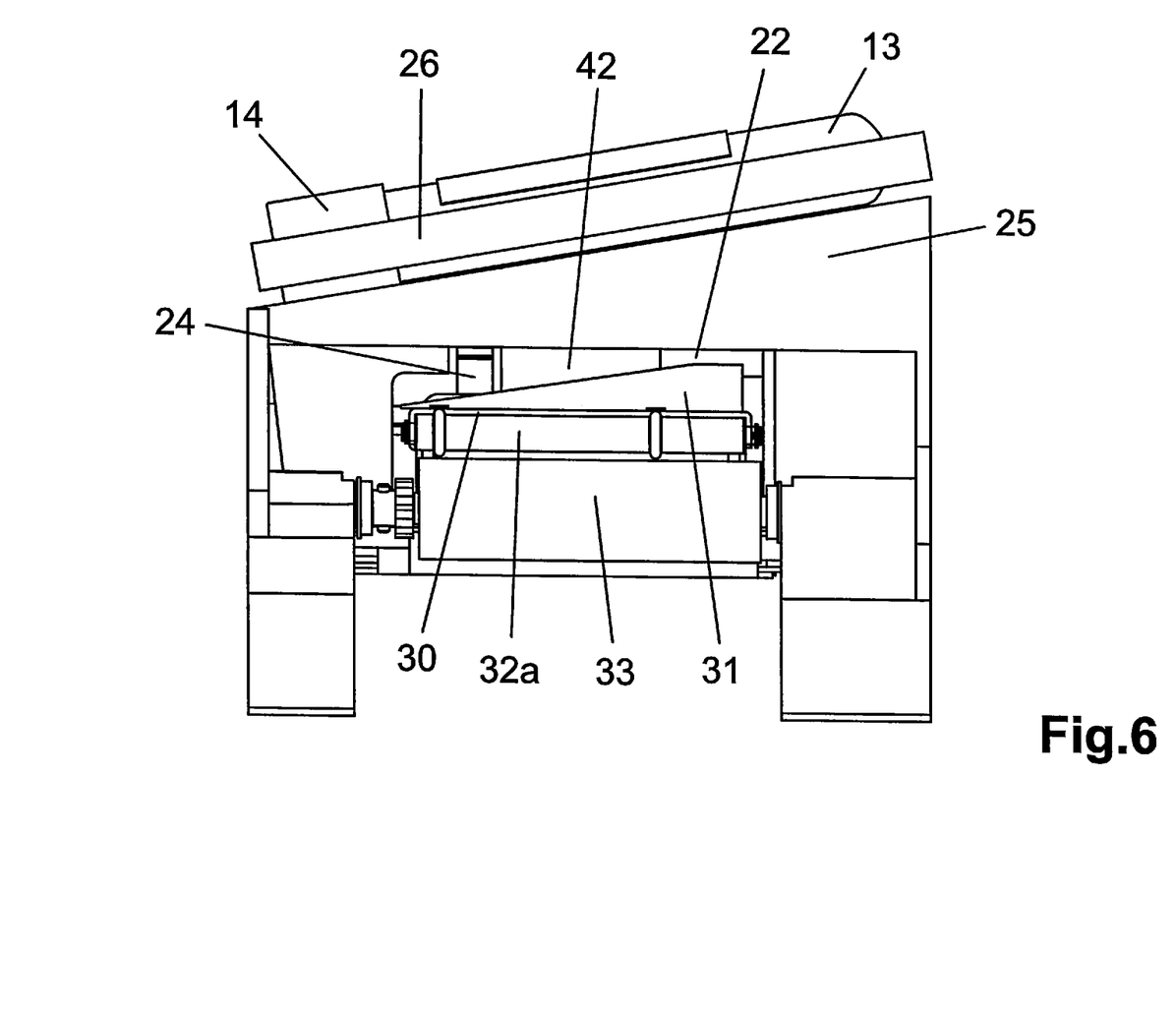
FIG. 6 is the same detail in FIG. 5, but in front view.
Figure 7:
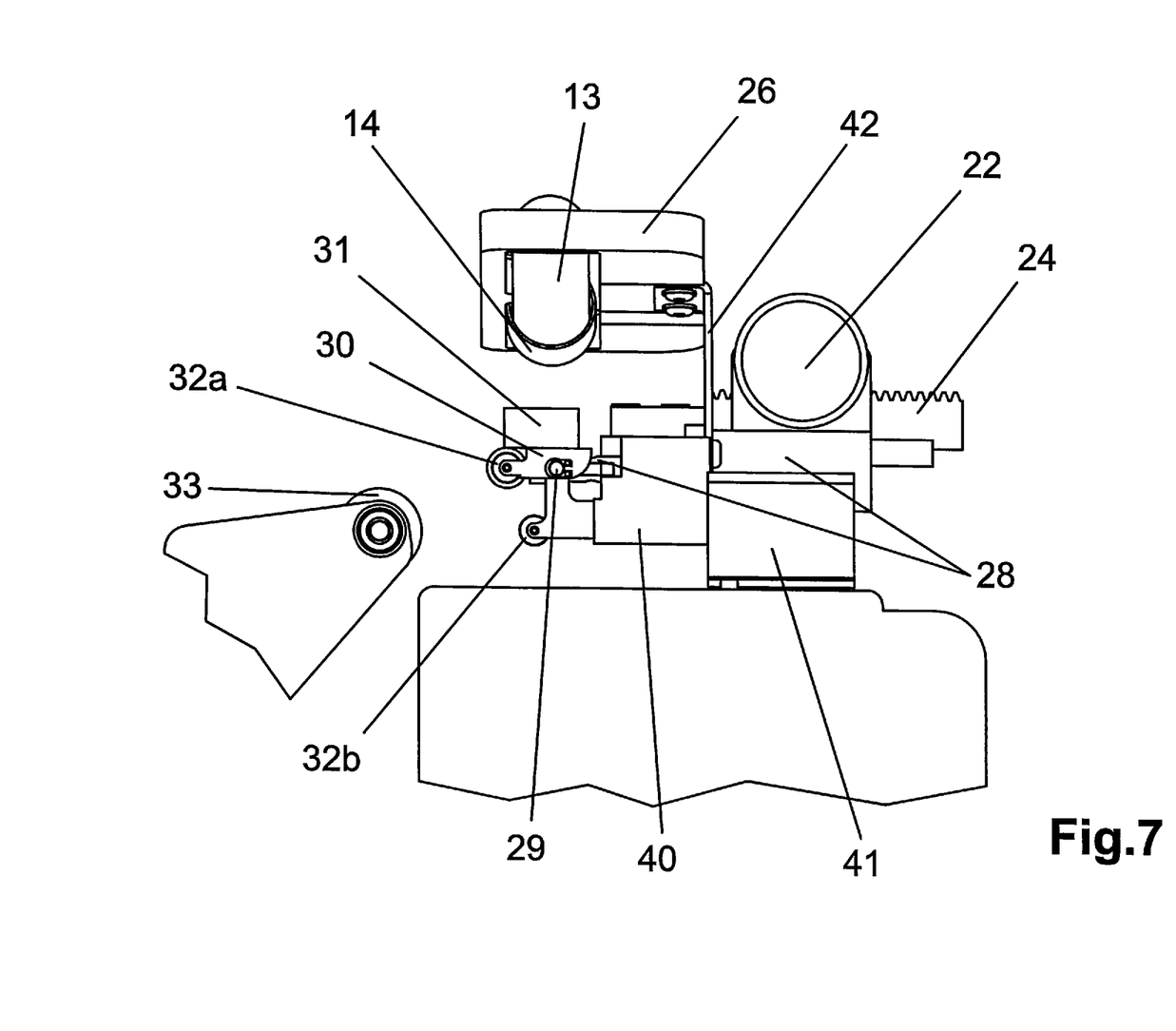
FIG. 7 is again a detail of the elements shown in FIGS. 5 and 6, in a covers the structure.

The first presence sensor 15 (FIG. 4, in which the test tube has been removed) detects the presence of test tube 13 and controls the actuation of electric motor 22, which thus starts, by controlling the anticlockwise rotation of pinion 23 (FIGS. 5-7 show the configuration in a step immediately prior to starting the motor). Therefore, rack 24 is displaced forwards along with all the elements which are integral therewith, i.e. element 41, block 40, bracket 42 and inclined compartment 26. It is the forward movement of the compartment 26 which releases the test tube 13 from the rest on the grooved housing 27, making it fall into the hole obtained in the body structure 25.

At this point, test tube 13 is accommodated for a few instances on the oblique chute 31, also previously moved forward, as integral with the forward movement of block 40. The motion of motor 22 is then reversed: perspective in FIG. 5), and the rack 24 and all the components integral therewith retract. Therefore, chute 31 retracts and the test tube 13 abuts against the structure body 25 falling into the working area itself.

Soon after, the motion of the motor is reversed once again, so that the group of components integral with one another are displaced forwards; in particular, the secondary rollers 32a and 32b entrap the test tube 13, jointly with the main roller 33 on the other side. Thus, such a group of components stops essentially midway with respect to the previous movement performed during the falling of test tube 13 onto the oblique chute 31; in particular, the inclined compartment 26, the opening of which accommodates a possible second test tube to be processed afterwards, stops midway during this step.

Meanwhile, the test tube 13 being processed is imperceptibly lifted by the action of the rollers which compress it, and the sensors integrated on the single board (FIG. 4) start reading operations.

Sensor 16 recognizes the color of the cap 14 of the test tube 13, check sensor 17 confirms the presence of the test tube, and length sensor 19 detects whether the test tube 13 is long or short.

At the same time, the rotation of the motorized main roller 33 is started (anticlockwise in the view in FIGS. 7-9) so that the test tube 13 rotates clockwise and the label presence sensor 18 can also work. During this step, the two secondary rollers 32a and 32b also rotate anticlockwise, but as mentioned they rotate passively only and by virtue of the rotation imparted onto the test tube 13 by the main roller 33. In practice, they serve the purpose of only containing the test tube 13 against the main roller 33, while ensuring adherence to such a roller.

In detail, the color sensor 16 of cap 14 comprises a light emitter 20 and a receiver 21, which measures the intensity of the RGB (Red-Green-Blue) color components present in the detected light, thus establishing the color of cap 14. same type, i.e. reflective infrared sensors: a diode continuously emits an infrared radiation, which is reflected towards a phototransistor by the presence of objects possibly placed immediately close to the sensor. Thus, for the check sensor 17, radiation is simply reflected by the presence of the test tube 13; for the label presence sensor 18, the reflection occurs when sensor 18 encounters the label while the test tube 13 rotates. Finally, for the length sensor 19, the radiation is reflected if a long test tube is present, while sensor 19 does not detect anything if the test tube is short.

In particular, it is worth dwelling on the label presence sensor 18. Indeed, the test tubes present on the market are already provided with a label applied onto the side body of the test tube containing some information related to the possible reactant contained in the test tube which determines the test class for which they are used, for example.

Therefore, the new label 10 which is produced must be superimposed on such a label which is already present.

The label presence sensor 18 identifies, during the rotation of the test tube 13 on the axis thereof, the area occupied by the pre-existing label by scanning the side wall of the test tube 13 itself, thus identifying the starting point of the label and the area occupied by the same.

Once the position of the label has been identified on the test tube 13, the rotation of the main roller 33 is interrupted, stopping the test tube 13 in a position so that the produced label 10 emitted through a slot can adhere to the test tube 13 and be superimposed on the pre-existing label.

The operations on the test tube 13 may proceed if the shape and color features of the cap 14 of the test tube 13 detected by the combined action of the sensors (in particular, sensors 16, 17 and 19) correspond to one of the expected features (displayed the monitor of PC 4).

Figure 10:
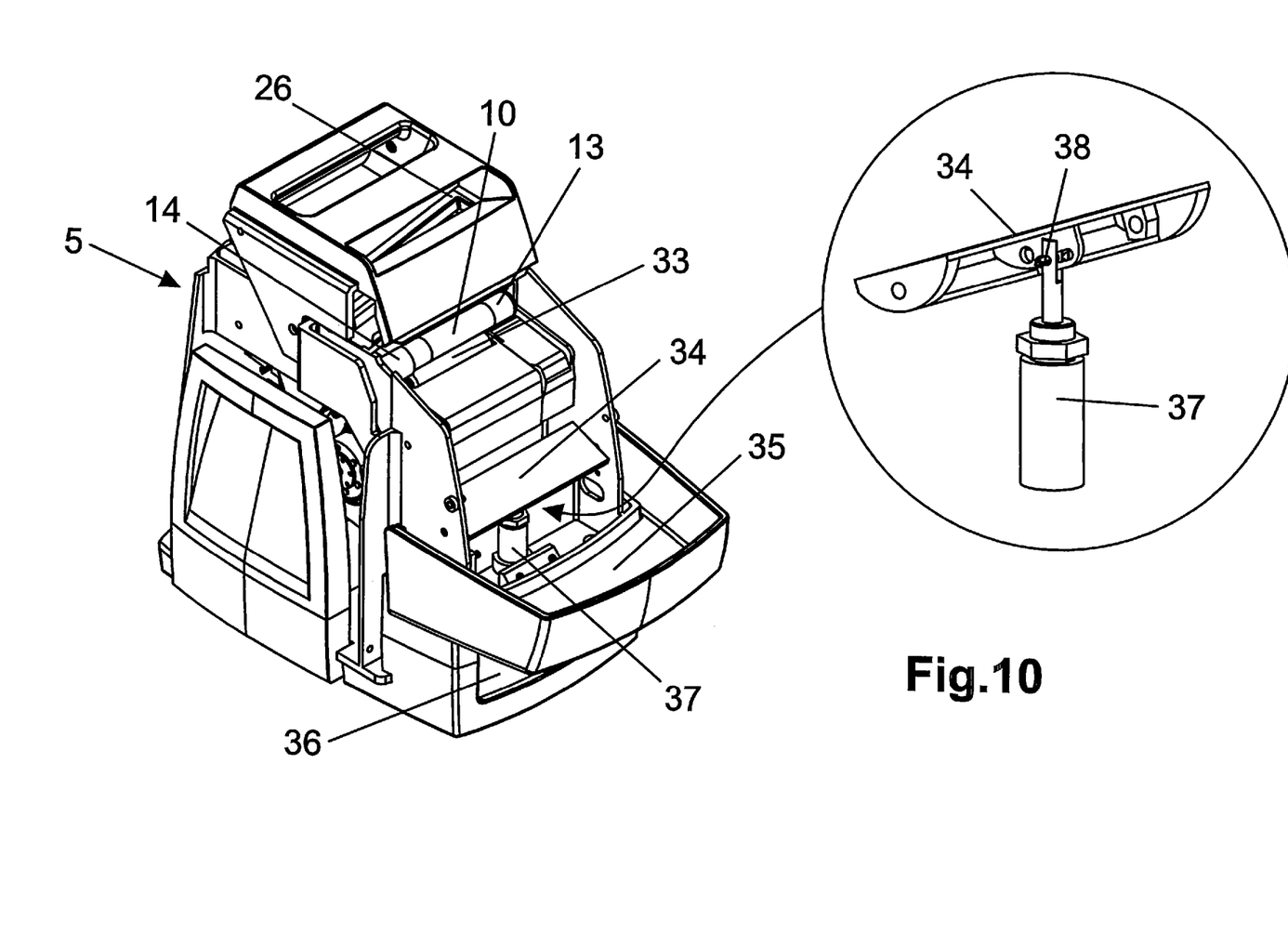
FIG. 10 shows the outer casing of the labeling machine once again, showing in particular the routing system of the correctly processed or rejected test tubes from another angle.

Otherwise, the non-conformity of the test tube present with respect to the expected features is detected, and the test tube must thus be rejected (an occurs by controlling, again by means of the processing and control board 6, the energizing of the second electromagnet 37, the upper tip of which retracts: by virtue of the presence of pin 38 which crosses the upper tip of electromagnet 37 and slides along a slot obtained in the profile of lever 34, the lever itself reverses its inclination so that, once the test tube has been expelled without having been labeled, it falls onto the lever, which has reversed its inclination and ends up in an opening behind, which leads into the second collection tray 36 (FIG. 10).

Failure of a test tube 13 to comply with an expected type of test tube may occur, for example, if the operator incorrectly loads either a test tube with an unexpected cap color or a test tube with a correct cap color, the size of which does not correspond to that associated with a given cap, or yet again a test tube positioned upside-down, the cap of which is thus not detected; in general, all those situations in which there is an upstream operator error.

The human error is indeed solved by expelling the non-conforming test tube.

As mentioned, in the case of correspondence with one of the expected test tubes, the processing and control board 6 is activated so that the procedure of printing the label 10 can start.

Printer 11 thus produces a label 10 having a barcode which contains the information needed to identify the biological material specimen and some wording with information useful for operators, such as for example, the name of the patient to which the specimen refers, the tests to be performed and the physical features of the test tube, identified by the system before the step of labeling.

The procedure with which the label 10 is stuck onto the test tube includes that, after having been produced by printer 11, its upper edge is detached from the paper of the wound ribbon 9 and made available in a The roller 33 itself then starts rotating anticlockwise (again with reference to FIG. 8), while causing a rotation in the opposite direction, i.e. clockwise, of the test tube 13, with respect to the direction in which it previously rotated when searching for the pre-existing label. Thereby, label 10 is essentially dragged, inserting itself in the imperceptible space between the main roller 33 and the test tube 13. It is worth noting that the operation of printing he label 10 and the subsequent rotation of the main roller 33 and the test tube 13 are perfectly coordinated; this promotes a safe adhesion of label 10 onto test tube 13, thus preventing the upper edge of label 10 from remaining suspended excessively long before being dragged by the rotation of roller 33, which could cause an unexpected bending and therefore improper sticking onto the test tube 13 (label not perfectly adherent to the test tube or not straight).

Furthermore, during the rotation of test tube 13, it is not displaced vertically, i.e. the only movement of interest is a rotation about its axis, and there is no risk of falling and consequent misalignment of the test tube 13 itself (and this also applies in the previous step of searching for the edge of the pre-existing label).

The operation ends after the test tube 13 has performed a given number of turns on itself, generated by the anticlockwise rotation of the main roller 33 (and, indirectly, also by the two passive secondary rollers 32a and 32b), and such that the produced label 10 can be deemed certainly stuck onto the test tube 13.

At this point, the motion of the electric motor 22 is reversed once again, so that the entire group of components integral with the rack 24 is displaced backwards, and in particular the secondary rollers 32a and 32b are detached from the test tube 13. Simultaneously, the main roller 33 stops.

The first electromagnetic 28 is energized during this step: it retracts its thinner end (i.e. the one on the left in FIGS. 7-9) which is released from pin secondary roller 32a connected thereto) could not rock because the left end of the electromagnetic 28 engaging pin 29 was underneath it, it is now no longer restrained and may bend.

Rack 24 and the group of components integral therewith is then moved forward again; at the same time, the main roller 33 starts moving again and thus, additionally, the test tube 13 and the secondary rollers 32a and 32b also move again.

The upper secondary roller 32a is now idle, i.e. as mentioned no longer restrained to move only in the longitudinal direction, and it lifts with its rotary movement on the side surface of the test tube 13 (FIG. 9), thus applying a trampoline-like effect onto the test tube 13, so that the test tube 13 slides along the main roller 33 and is expelled, falling firstly onto lever 34 and from here into the first collection tray 35 (FIG. 10).

Concurrently with such an expulsion, a possible further test tube which is waiting to be processed in the inclined compartment 26, falls onto the oblique chute 31 so that the labeling cycle can start, obviously once electromagnet 28 has been de-energized, which thus returns to engage pin 29 and block the rocking movement of shelf 30 again.

It is therefore worth noting that the loading mechanism of the test tubes into the labeling machine is of the "one-by-one" type (sequential loading, i.e. one test tube at a time).

It is worth noting that a thrust no higher than that of the previous steps is applied to expel the test tube 13, only because the releasing of the electromagnet 28 from pin 29 allows the upper secondary roller 32a to be lifted and thus exert a trampoline-like action onto the test tube 13.

The disclosed steps are repeated until all the required test tubes have been labeled. At the end of the cycle of labeling such test tubes, the operator collects them from the collection tray 35 and proceeds by collecting the biological material (blood or other) from the patient. to the labeling machine 5 and passes the filled test tubes one by one under the barcode reader 39 (FIG. 2) to confirm completion of the labeling and collecting operations on each single test tube 13 and to check compliance with expected results; indeed, the barcode reader 39 communicates with the processing and control board 6, which checks that there are no discrepancies between the barcode printed on each label and the one expected for each test tube, sanctioning the end of the operating cycle on the required test tubes.

Such an operation is further particularly important because the passage of each single test tube under the barcode reader 39 also allows the processing and control board 6 to record the exact time at which the specimen was collected; this information are sent to the database of the LIS 3, and may be cross-referenced, if needed, with those from the devices which perform the test on the biological specimen at a later step. Indeed, the test devices are also advantageously capable of communicating the exact time at which they processed a given specimen to the database of the LIS 3, and during final diagnosis the doctor may determine whether the test is significant or not, and therefore ask for the test to be repeated, by inferring the time which elapsed between collection and testing.

The processing and control board 6 which is integrated in the labeling machine 5 has a univocal IP network address in the local computer network 50; thus, communication with the labeling machine 5, or rather with the application residing on the processing and control board 6, is possible for the operator working on it and any other operator equipped with a PC connected to the network 50, simply by typing the univocal network address of the labeling machine 5 itself into an Internet browser.

This allows to control the operations of the labeling machine 5 without needing to use a PC on which any specific software application is installed, with the further evident advantage (particularly for a central computer possibly present at the laboratory) to connect in different moments to the Furthermore, a traceability engine 7 capable of communicating the machine state of the labeling machine 5 to an external server 8 at any time is present on the processing and control board 6. Extending this feature to all the labeling machines present on the network, any operation performed on any labeling machine is recorded on such an external server 8, which may thus work, if needed, as historical archive for retrieving data, indicating which operations were performed on the test tubes associated with a given patient on a specific date.

Advantageously supposing that the external server 8 records the operations performed by the various test devices in the same manner, it is possible to keep track of the various types of tests carried out on each patient's specimens on a given date.

The innovative aspect of the invention is thus in using a processing and control board 6 inside the labeling machine 5, instead of an application residing on the PC 4 with which the operator in charge of collection is equipped, this feature being conductive to better control during all steps of operation of the labeling machine 5, both in terms of mechanical component actuation and, above all, in terms of checking compliance with expected data during the entire operating cycle, i.e. checking that the label 10 with the correct barcode is actually stuck to a given test tube 13, as established beforehand by the processing and control board 6 itself by communicating with the database 3 of the LIS. This all eliminates any risk of error (incorrect test tube labeling), thus solving other possible, unpredictable human errors by the operator by expelling the incorrect loaded test tubes before they are labeled.

Furthermore, having the application integrated within the labeling machine 5 contributes, as compared to the known solutions, to making the labeling machine itself an active instrument capable of querying the database 3 of the LIS and thus no longer a simple passive executor of orders. board 6 provided with its own univocal network address allows the hospital/laboratory operators to also connect to the labeling machine 5 remotely if they can access the local computer network 50, thus managing machine state and operations thereof; thereby, it is no longer necessary to equip each single PC 4 interfaced with a labeling machine 5 with a specific application to be installed, but it will suffice for the PC 4 to have a navigation browser in which to enter the IP address of the labeling machine 5; each operator may additionally go from managing one labeling machine to the other by varying such an IP address.

Thereby, the solution can be adapted in any manner regardless of the operating system in use on the PC 4 with which the operator is equipped.

Furthermore, the synchronization of the operation of the barcode printing on the label 10 and the application of the label onto test tube 13 avoids any risk of incorrect application (twisted or folded label), which could have consequences if the barcode needs to be later read by test modules to which the labeled test tubes 13 are then transferred.

It is thus an innovative aspect of the invention even the presence of a barcode reader 39 aboard the labeling machine 5 which, at the end of the operating cycle on a given number of test tubes, checks the compliant labeling of the test tubes 13 present in the collection tray 35, verifying the correspondence thereof with expected data contained in the processing and control device 6, so that the time at which the labeling cycle ends, and subsequently the collection of biological material, is appropriately recorded for each single test tube.

The invention thus described is susceptible to many changes and variants, all included within the scope of the inventive concept.

In practice, the materials used as well as the shapes and dimensions may be any, according to needs.

The invention claimed is:

1. An apparatus for identifying a patient and marking containers of biological products or test tubes associated to said patient before collecting said biological products to be analyzed, comprising:
   a high security portable hardware device for processing and storing the patient's data capable of associating the patient's personal data and biometric data,
   a reading and patient biometric recognition device of said portable hardware device,
   a personal computer interacting with an operator and connected to a local communications network for exchanging information with remote data storage means,
   one or more computerized labeling machines of test tubes, each comprising a printer of barcodes onto labels adapted to receive printing commands after comparing expected and detected specimens accommodated in a positioning and recognition device supported by said labeling machine and applying said labels to said test tubes,
   each of said labeling machine comprises a motorized main roller and an upper and a lower passive secondary rollers, the upper and the lower passive secondary rollers are able to move forward and backwards with respect to the motorized main roller to entrap the test tube, the motorized main roller rotating and causing a rotation in the opposite direction of the test tube by two passive secondary rollers, the label being essentially dragged, inserting itself in the imperceptible space between the motorized main roller and the test tube, the operation of printing the label and the subsequent rotation of the motorized main roller and of the test tube being perfectly coordinated in order to promote a safe adhesion of label onto the test tube, wherein each of said labeling machines comprises a processing and control board provided with a univocal address within said local communications network, said processing and control board being capable of exchanging information with said remote data storage means and with said personal computer, and on the basis of said information, as well as that received after said comparison operated by said positioning and recognition device, of sending said print commands to said printer comprised in said labeling machine, and wherein the upper passive secondary roller is rocking to lift on the side surface of the test tube after the adhesion of the label and the upper and the lower passive secondary rollers move together forward towards the motorized main roller while it rotates to expel the test tube by sliding along the motorized main roller.

2. The apparatus according to claim 1, wherein each labeling machine comprises a traceability engine inside said processing and control board, which communicates the state of each said labeling machines in each instant to an external server, said external server storing data and thus serving in case of need as historical archive for the retrieval of said data.

3. The apparatus according to claim 1, wherein each of said labeling machines comprises a processing and control board integrating an application that, if biometric data detected in real time on the patient by said reading and patient biometric recognition device coincides with biometric data of the same patient stored into the high security portable hardware device, queries the remote data storage means twice, firstly to recall the personal data of the patient associated with the detected biometric data from the remote data storage means, and then to extract the list of the test to be performed entered into remote data storage means associated with the patient.

4. The apparatus according to claim 1, wherein said positioning and recognition device comprises an inclined compartment for accommodating a test tube positioned by an operator, said inclined compartment translating horizontally in manner integral to the movement of a rack actuated by an electric motor, a first presence sensor of said test tube, a color sensor of the cap of said test tube, a second presence sensor of said test tube, a presence sensor of a pre-existing label and a length sensor of said test tube.

5. The apparatus according to claim 1, wherein said main roller and said two passive secondary rollers are adapted to turn said test tube during the search of a pre-existing label and the application of said label.

6. The apparatus according to claim 1, wherein a first electromagnet is able, if energized, to release itself from a pin of said secondary passive roller allowing the lifting of said upper passive secondary roller during the step of expulsion of said test tube.

7. A labeling machine suitable for marking containers of biological products or test tubes, comprising a barcode printer on labels adapted to receive printing commands after comparing expected and detected test tubes accommodated in a positioning and recognition device supported by said labeling machine and to apply said labels onto said test tubes, wherein it comprises a motorized main roller and an upper and a lower passive secondary rollers, the upper and lower passive secondary rollers are able to move forward and backwards with respect to the motorized main roller to entrap the test tube, the motorized main roller rotating and causing a rotation in the opposite direction of the test tube by two passive secondary rollers, the label being essentially dragged, inserting itself in the imperceptible space between the motorized main roller and the test tube, the operation of printing the label and the subsequent rotation of the motorized main roller and of the test tube being perfectly coordinated in order to promote a safe adhesion of label onto the test tube, wherein the upper passive secondary roller is rocking to lift on the side surface of the test tube after the adhesion of the label and the upper and the lower passive secondary rollers move together forwards towards the motorized main roller while it rotates to expel the test tube by sliding along the motorized main roller.

8. The labeling machine according to claim 7, wherein said positioning and recognition device comprises an inclined compartment for accommodating a test tube positioned by an operator, said inclined compartment translating horizontally in manner integral to the movement of a rack actuated by an electric motor, a first presence sensor of said test tube, a color sensor of the cap of said test tube, a second presence sensor of said test tube, a un presence sensor of a pre-existing label and a length sensor of said test tube.

9. The labeling machine according to claim 7, wherein a first electromagnet being capable is able, if energized, to release itself from a pin of said secondary passive roller allowing the lifting of said passive secondary roller during the step of expelling said test tube after it has been labeled.

10. The labeling machine according to claim 7, wherein it comprises a barcode reader for reading and confirming the end of operation, after collecting, on each of said labeled test tubes.

11. The labeling machine according to claim 7, wherein it comprises a lever and a first and a second collection trays, the lever routes the correctly labelled test tube towards the first collection tray and the rejected test tubes towards the second tray after the step of expulsion of said test tube.

* * * * *